United States Patent

Nix et al.

[11] 4,247,631
[45] Jan. 27, 1981

[54] REAGENT AND METHOD FOR THE ANALYTIC DETERMINATION OF HYDROGEN PEROXIDE

[75] Inventors: Paul T. Nix, Jackson; Spencer Fields, Red Bank, both of N.J.

[73] Assignee: Millipore Corporation, Bedford, Mass.

[21] Appl. No.: 8,154

[22] Filed: Jan. 31, 1979

[51] Int. Cl.³ .......................... C12Q 1/62; C12Q 1/28
[52] U.S. Cl. ...................................... 435/10; 435/11; 435/14; 435/28; 435/810; 23/230 B
[58] Field of Search .................. 435/11, 14, 28, 810, 435/805, 10; 23/230 B; 252/408 R

[56] References Cited

U.S. PATENT DOCUMENTS

| Re. 29,498 | 12/1977 | Meiattini | 435/11 |
|---|---|---|---|
| 2,194,201 | 3/1940 | Eisenstaedt | 260/310 |
| 3,907,642 | 9/1975 | Richmond | 435/11 |
| 4,089,747 | 5/1978 | Bruschi | 435/28 |

FOREIGN PATENT DOCUMENTS 1385320   2/1975   United Kingdom ................. 435/11

OTHER PUBLICATIONS

Dunford et al., "Kinetics of the Oxidation of p-Aminobenzoic Acid Catalyzed by Horseradish Peroxidase Compounds I and II", J. Biol. Chem., 250 (8), 2920-2932, (1975).
Eisenstaedt; "The Condensation of Aminoantipyrine with Aromatic Amines in the Presence of Oxidizing Agents", J. Org. Chem., 3, 153-165, (1938).
Emerson; "The Condensation of Aminoantipyrine II; A New Color Test for Phenolic Compounds", J. Org. Chem., 8, 417-428, (1943).
Hall; J. W. et al.; "Automated Determination of Glucose Using Glucose Oxidase and Potassium Ferrocyanide", Analyt. Biochem., 26, 12-17, (1968).
Trinder; P., "Determination of Glucose in Blood Using Glucose Oxidase with an Alternative Oxygen Acceptor," Ann. Clin. Biochem. 6, 24-27, (1969).
Gochman N. et al.; "Automated Determination of Uric Acid, with Use of a Uricase—Peroxidase System," Clin. Chem., 17, (12), 1154-1159, (1971).
Gochman N. et al.; "Application of a New Peroxide Indicator Reaction to the Specific, Automated Determination of Glucose with Glucose Oxidase," Clin. Chem., 18, (9), 943-950, (1972).

*Primary Examiner*—Benoit Castel
*Attorney, Agent, or Firm*—Kenyon & Kenyon

[57] ABSTRACT

A 3-aminobenzoic acid or a 3-aminobenzenesulfonic acid, when reacted with a 4-aminoantipyrine in aqueous medium in the presence of hydrogen peroxide forms a novel colored dye which is believed to be a charge-transfer complex of free radicals formed from the 3-aminoaromatic acid and the 4-aminoantipyrine. The dye and the process by which it is produced are useful in analytical procedures for hydrogen peroxide, as well as in enzymatic analyses involving the formation of hydrogen peroxide.

37 Claims, No Drawings

REAGENT AND METHOD FOR THE ANALYTIC DETERMINATION OF HYDROGEN PEROXIDE

The present invention relates to a reagent and method which are useful for the analytic determination of hydrogen peroxide. More particularly, the present invention is concerned with a new chromogen reagent for and its use in an enzymatically coupled analytic determination of hydrogen peroxide.

BACKGROUND

A variety of methods for the analytic determination of hydrogen peroxide have been known. One class of such methods involves the use of the enzyme peroxidase to catalyze the reaction of a substrate with hydrogen peroxide to oxidize the substrate and form water. Enzymatic determinations of this type have found particular utility in the analysis of various substances, such as cholesterol, glucose and uric acid, in body fluids such as blood. In such methods, the body fluid is admixed with an enzyme capable of catalyzing oxidation of the substance to be determined with the concurrent formation of hydrogen peroxide. The fluid also is admixed with peroxidase and a substrate for peroxidase which, on oxidation, undergoes a color change. The extent of the color change is a measure of the amount of hydrogen peroxide formed, which in turn is a measure of the substance to be determined.

For example, Hall et al, in "Automated Determination of Glucose Using Glucose Oxidase and Potassium Ferrocyanide", Analyt. Biochem., 26, 12-17 (1968), describe a method for the quantitative determination of glucose by oxidation with glucose oxidase to form gluconic acid and hydrogen peroxide, and reduction of the hydrogen peroxide with potassium ferrocyanide in the presence of peroxidase to form ferricyanide. Trinder, in "Determination of Glucose in Blood Using Glucose Oxidase With an Alternative Oxygen Acceptor", Ann. Clin. Biochem., 6, 24-27 (1969), described the use of phenol and 4-aminophenazone (4-aminoantipyrine) as the color-forming system in place of the potassium ferrocyanide. In this system, it is believed that the phenol is oxidized and then reacts with the 4-aminophenazone to form a quinonimine dye; a reaction which previously had been described by Emerson in "The Condensation of Aminoantipyrine II. A New Color Test for Phenolic Compounds", J. Org. Chem., 8, 417-28 (1943) and in U.S. Pat. No. 2,194,201 granted Mar. 19, 1940. Still more recently, Meiattini, in U.S. Pat. No. 3,866,045, granted May 27, 1975 (Re. U.S. Pat. No. 29,498 granted Dec. 20, 1977) applied the reactants described by Emerson to the Trinder reaction.

This type of procedure can be employed to determine other constituents of blood or other body fluids by replacing glucose oxidase with an enzyme capable of catalyzing the oxidation of another component, e.g., cholesterol oxidase or uric acid oxidase (uricase), with concurrent formation of hydrogen peroxide. For example, the adaptation of this procedure to the determination of serum uric acid is described by Trivedi et al in "New Enzymatic Method for Serum Uric Acid at 500 nm", Clin. Chem., 24, (11), 1908-11 (1978). However, the Trinder-type chromophore is not as sensitive as is desired for the determination of metabolites such as uric acid, which ordinarily are present in blood in very low concentrations, e.g., of the order of 4 to 9 mg/100 ml of blood, as compared with concentrations of 80-100 mg/100 ml for glucose and 150-250 mg/100 ml for cholesterol.

Another type of chromogen-chromophore system which has been employed as a hydrogen peroxide detector in analytical procedures of this type is the 3-methyl-2-benzothiazolinone hydrazone/N,N-dimethylaniline system, in which the two reagents oxidatively couple to form a covalently bonded indamine dye. The application of this procedure to the analysis of uric acid and glucose was reported by Gochman et al in "Automated Determination of Uric Acid, With Use of a Uricase-Peroxidase System", Clin. Chem., 17, (12), 1154-59 (1971) and "Application of a New Peroxide Indicator Reaction to the Specific, Automated Determination of Glucose with Glucose Oxidase", Clin. Chem., 18, (9), 943-50 (1972).

THIS INVENTION

The present invention is concerned with a new chromogen-chromophore system for the enzymatic determination of hydrogen peroxide. More particularly, this invention is concerned with a new chromogen-chromophore system capable of use in the enzymatic determination of blood components via the intermediate formation of hydrogen peroxide, and which, due to the unusually high extinction coefficient of the chromophore, has the requisite sensitivity for the determination of components, such as uric acid, which normally are present in low concentration.

Accordingly, it is an object of this invention to provide a new reagent and method for the determination of hydrogen peroxide.

It is a further object of this invention to provide a new reagent and method for the enzymatically-coupled determination of hydrogen peroxide.

Still another object of this invention is the provision of a new reagent and method for the determination of components of body fluids via enzymatic formation of hydrogen peroxide as an intermediate, followed by enzymatically-coupled determination of the thus-formed hydrogen peroxide.

These and other objects of this invention, which will be apparent from the ensuing specification and claims, are achieved by contacting hydrogen peroxide with, as a chromogen, a mixture of a 3-aminoaromatic acid, as hereinafter defined, and a 4-aminoantipyrine, as hereinafter defined, under conditions sufficient to form a novel colored dye, or chromophore.

The aminoaromatic acid which is employed in accordance with this invention is either a 3-aminobenzoic acid, or 3-aminobenzenesulfonic acid. Such acids may be represented by the structural formula:

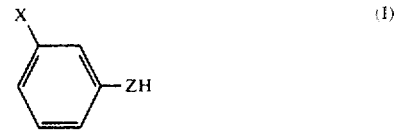
(I)

wherein X is a mono- or a dialkylamine group and ZH is the carboxyl ($-CO_2H$) or sulfo ($-SO_3H$) group. The nature of the alkyl group of the alkylamine group is not critical, provided it permits formation of the desired dye. Consequently, for reasons which will become apparent from the ensuing discussion, bulky groups such as tertiary-alkyl or cycloalkyl groups should not be employed. Primary alkyl groups are preferred. The length of the alkyl group is not critical, so long as the aminoaromatic acid and the resulting dye are soluble in aqueous media. However, lower alkyl groups, i.e., alkyl groups of from about 1 to about 6 carbons, e.g., methyl, ethyl, propyl, butyl, pentyl and hexyl are preferred. Dialkylamino groups are preferred, with the dimethylamino group being especially preferred. The aminoaromatic acids may be substituted on the aromatic (i.e., the benzene ring), provided the substituent does not interfere with the formation of the dye. For example, one or more halogen atoms, e.g., chlorine or bromine atoms, may be present. It is believed, however, that no non-labile substituent, such as alkyl, should be present on the position para to the amino group.

The second component of the reagent of this invention is a 4-aminoantipyrine, which may be represented by the formula:

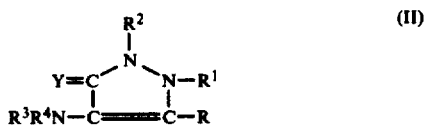

wherein each of R and R¹, when taken separately, is alkyl, R² is an aromatic radical, each of R³ and R⁴, when taken separately, is hydrogen or alkyl, and Y is oxygen or sulfur. As was the case with the aminoaromatic acid, the alkyl groups of the aminoantipyrine (i.e., the R, R¹, R³ and R⁴ substituents), should not be bulky groups, such as tert-alkyl, and their chain length is limited by the solubility of the aminoantipyrine and the resulting dye. Lower alkyl groups, especially the methyl group, are preferred. It is desirable that the 4-amino group be primary amino, i.e., that both R³ and R⁴ be hydrogen, because the use of such compounds affords a more rapid reaction and a more intense color. The aromatic radical represented by R² is preferably phenyl or substituted phenyl. The phenyl substituents are desirably lower alkyl or halogen. The preferred 4-aminoantipyrine reagent is 4-aminoantipyrine.

The dye formed upon contacting the mixture of the aminoaromatic acid (I) and aminoantipyrine (II) with hydrogen peroxide is not a quinonimine type of the type formed according to Trinder, Emerson and Meiattini. The dye of these references requires the presence of an unsubstituted 4-amino group on the aminoantipyrine and leads to the formation of a covalently bonded species in accordance with the following equation:

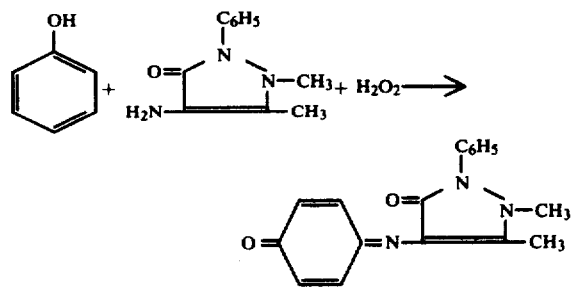

Emerson, in his U.S. Pat. No. 2,194,201, as well as in his earlier paper (Eisenstaedt), "The Condensation of Aminoantipyrine With Aromatic Amines in the Presence of Oxidizing Agents," J. Org. Chem. 3, 153–65 (1938), also described the reaction of aminobenzenes, e.g., aniline and dimethyl aniline, with 4-aminoantipyrine, but again a covalently bonded dye is formed and the 4-amino group of 4-aminoantipyrine must be unsubstituted.

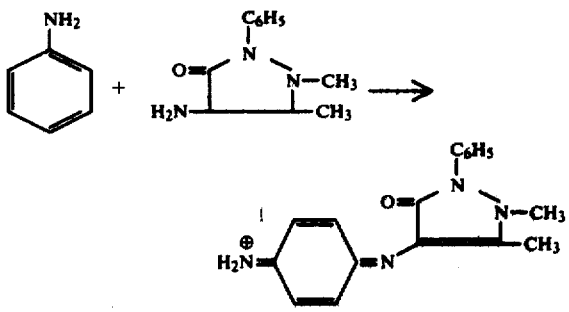

In contrast, the dye of the present invention is formed even when the 4-amino group of the aminoantipyrine is substituted. For example, when 3-(dimethylamino)benzoic acid is reacted, in the presence of hydrogen peroxide and peroxidase, with either 4-aminoantipyrine or 4-(dimethylamino)antipyrine, a blue dye having maximum absorbance at 550 nm is formed. When phenol or sodium p-hydroxybenzoate is substituted for the 3-(dimethylamino)benzoic acid, a red dye having maximum absorption at 500 nm is formed with 4-aminoantipyrine, but substantially no reaction is seen with 4-(dimethylamino)antipyrine. According to Emerson (Eisenstaedt), the reaction of N,N-dimethylaniline with 4-aminoantipyrine forms an imino dye, while substitution of 4-(N,N-dimethylamino)antipyrine for 4-aminoantipyrine leads only to the formation of blue colored oxidized 4-(N,N-dimethylamino)antipyrine.

The dye product formed with 3-(dimethylamino)benzoic acid in accordance with this invention is more soluble in water than are the covalently bonded imine dyes formed from phenol, sodium p-hydroxybenzoate or dimethylaniline. On the other hand, it is less soluble in organic solvents, such as chloroform or cyclohexane, than are the imine-type dyes.

In view of this evidence, it is believed that the dye formed in accordance with this invention is a charge-transfer complex of an aminoaromatic acid free radical and a 4-aminoantipyrine free radical, as represented by the respective formulae (I-A) and (II-A):

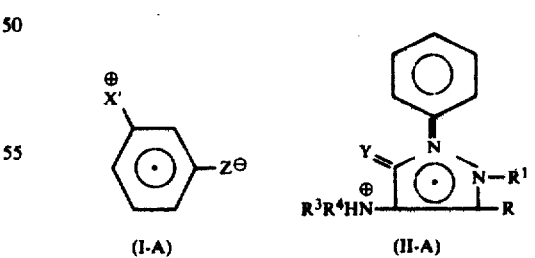

wherein X' is an alkylimino or a dialkylimino group, Z is the residue formed by removal of hydrogen from a carboxyl or sulfo group, and Y, R, R¹, R³ and R⁴ are as defined above. The precise structure of the complex has not been definitively established; however, the following structures, as illustrated by the complex formed from 4-(N,N-dimethylamino)antipyrine and 3-(dimethylamino)benzoic acid, are possible.

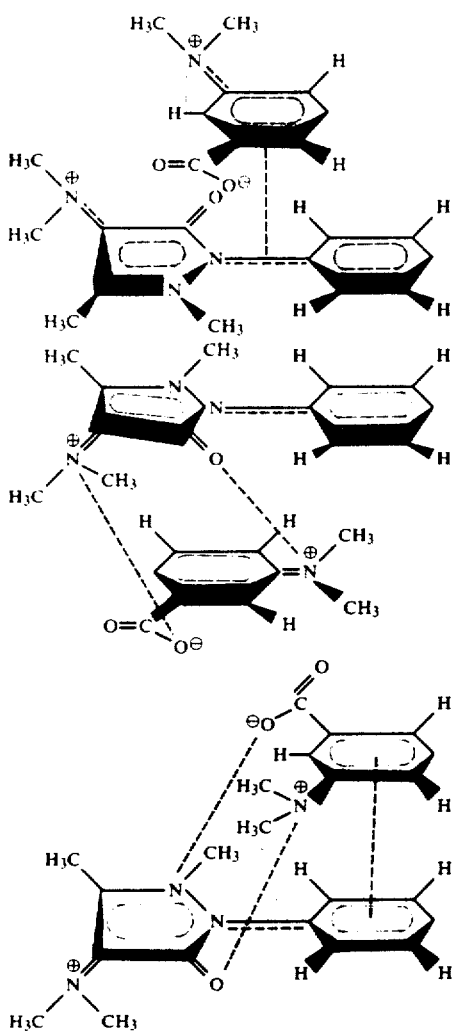

If the foregoing theory is correct, it will be seen that bulky substituents on either moiety can interfere with, and may even prevent, the formation of a charge transfer complex, and it is for this reason that such substituents are not desired. Regardless of theory, it is clear that the dye formed in accordance with the present invention is not the imine-type dye of the prior art.

It is possible that a charge-transfer complex of this type may be formed as an intermediate in the reaction of N,N-dimethylaniline with 4-aminoantipyrine described by Emerson (Eisenstaedt), and may have been responsible for the blue color reported by Eisenstaedt with 4-(N,N-dimethylamino)antipyrine. However, N,N-dimethylaniline is not suitable for use in an analytical reagent system. In the first place, its rate of reaction is slower than that of the aminobenzoic acids employed in accordance with this invention. Moreover, dimethylaniline is an oily liquid which is not highly miscible with water or aqueous media. Consequently, the rate of dye formation is non-linear, which as a practical matter precludes the use of dimethylaniline in an analytical system.

The dyes formed by the reaction of the aminoaromatic acid (I) and of the aminoantipyrine (II) generally have absorption maxima in the range of from about 450–650 nm. They also are characterized by high extinction coefficients. For example, the dye obtained from 3-(N,N-dimethylamino)benzoic acid and 4-aminoantipyrine has an absorption maximum at 550 nm, and an extinction coefficient of $1.72 \times 10^4$ 1 mole$^{-1}$ cm$^{-1}$. It is this very strong absorption which permits these dyes to be used in analyses for detecting even small concentrations of hydrogen peroxide. Thus, these dyes can be employed to analyze for components of body fluids which are present in low concentrations, either because they normally are present in small amounts (e.g., uric acid in blood), or because the body fluid has been diluted prior to analysis.

The dyes of this invention are less stable than the imine dyes formed in accordance with the teachings of Trinder, Emerson and Meiattini. The dyes of the prior art references are extremely stable, covalently bonded compounds capable of use as dye stuffs. The dyes of this invention, in contrast, while sufficiently stable to be useful in an analytical procedure, do decompose within a comparatively short period of time.

Because of the relatively short life of the dye, the concentration of the dye in the reaction mixture varies with time. Initially the concentration increases to a maximum concentration, following which the concentration of the dye decreases. The rates of formation and decomposition of the dye, as well as the time at which the maximum concentration of dye is reached, are dependent upon the reaction conditions, including in particular the proportion of the acid (I) to the antipyrine (II), the absolute concentrations of these reactants, and the reaction temperature. Thus, each of these variables must be adjusted to achieve the concentration of the dye desired for the analytical determination within the time period desired. Further, the time at which the dye concentration is at or near the maximum concentration may be varied to achieve a useful time span in which to detect the dye and perform the desired analysis.

The proportion of aminoaromatic acid (I) and 4-aminoantipyrine (II) employed in the reaction to form the dye are not narrowly critical, provided the desired dye is formed. In general, however, operable proportions will be within the range of from about 0.1 to about 25 moles of aminoaromatic acid (I) per mole of aminoantipyrine (II). The optimum proportion is largely a function of the desired rate of formation of the dye. As the ratio of acid (I) to antipyrine (II) increases, the rate of formation of the dye increases. However, due to the free radical nature of the reaction believed to be involved, an increased proportion of acid (I) also reduces the life of the resulting dye. Thus, the ratio of the two components must be adjusted to optimize the reaction rates, and to permit a determination to be made within a reasonable period of time and/or to form a maximum dye concentration having a useful life. The optimum ratio will vary, depending upon whether the amino group of the B 4-aminoantipyrine is substituted. A proportion of acid (I) to antipyrine (II) of about 10:1, i.e., from about 8:1 to about 12:1, is preferred when the 4-amino group is a primary amine group. When the amino group is a tertiary amino group, however, the optimum ratio of acid (I) to antipyrine (II) is less than 1:1, and preferably is about 0.25:1, i.e., from about 0.2:1 to about 0.3:1.

The concentrations of the two chromogens are those sufficient to form a measurable amount of dye. In general, the concentrations of the aminoantipyrine can be in the range of from about 0.01 to about 1000 millimoles per liter, and more particularly in the range of from about 0.1 to about 5 millimoles per liter. A concentration of aminoantipyrine in the range of from about 0.35 to about 0.5 millimoles per liter is preferred. The concentration of amino acid is that required to give a dye within the desired time period, and can vary from as low as 0.1 millimoles per liter up to the solubility limit, or about 50 millimoles per liter.

As is noted above, the reaction of the two chromogens with hydrogen peroxide is catalyzed by the enzyme peroxidase. As is well known, this enzyme is obtained from a variety of sources, including horseradish, liver, parsley and certain bacteria. Although the nature of the peroxidase obtained from the different sources does vary, the particular source of the peroxidase is not critical to this invention. However, horseradish peroxidase is the most common form of peroxidase, and for that reason horseradish peroxidase is preferred. The amount of peroxidase employed is not a feature of this invention, and amounts employed in the prior art procedures can be employed. In general, however, there are employed at least 50 units of peroxidase per liter of solution, and preferably at least 500 units per liter. In principle, there is no maximum amount; however, amounts of peroxidase in excess of about 2500 units per liter are unnecessary, and amounts in the range of from about 1200 to about 1600 units per liter are preferred.

The temperature at which the reaction takes place, as well as the pH of the reaction mixture, both affect the rate of dye formation and the stability of the dye. In general, the rate of reaction increases and dye stability decreases with temperature, with a temperature of about room temperature (i.e., from about 20° C. to about 45° C., and preferably from 25° C. to about 30° C.) being generally useful. Furthermore, as is well known, the activity of peroxidase is optimal at a pH of about 6.8, i.e., from about 6.5 to about 7.0.

When, however, the invention is employed as a part of an enzymatic analysis of a body fluid component, then the temperature and pH may have to be adjusted to optimize the overall reaction scheme. For example, when analyzing for cholesterol, a temperature of about 30° C. and a pH of about 7.5 are preferred; when analyzing for glucose a temperature of about 25° C. and a pH of about 7.0 are preferred; and when analyzing for uric acid, a temperature of about 25° C. and a pH of about 8.0 are preferred.

Because of the importance of pH to the enzymatic reactions, it is desirable to employ a buffer designed to maintain the desired pH for the period required to effect the analysis. Such buffers include phosphate, pyrophosphate, borate and other buffers well known to the art, such as tris(hydroxymethyl)-aminomethane ("tris"), N,N,N-tris(2-hydroxyethyl)methyl-2-aminomethane sulfonic acid ("TES"), N-(2-hydroxyethyl)piperazine-N'-2-ethane sulfonic acid ("HEPES"), N,N-bis(2-hydroxyethyl)glycine ("bicine"), N,N,N-tris(2-hydroxyethyl)methylglycine ("tricine"), piperazine-N,N-bis(2-ethane sulfonic acid) ("PIPES"), N,N-bis(2-hydroxyethyl)-2-aminoethane sulfonic acid ("BES") and the like.

When the present invention is employed for the analysis of a specific component of a body fluid, there is also employed an enzyme capable of catalyzing the formation of hydrogen peroxide by oxidation of the component in question. Such enzymes are known generally as "oxidases", and include glucose oxidase, cholesterol oxidase and uric acid oxidase. The amount of such oxidase is known to the art, and hence it is not a novel feature of this invention.

In one embodiment of this invention, an analytical kit or system is provided which contains the desired ingredients in predetermined proportions. The ingredients may be packaged separately, or two or more may be admixed. It is an advantage of this invention that both the aminoaromatic acid (I) and the aminoantipyrine (II) are stable solids. In such kits, the enzyme(s) are desirably packaged as dry solids.

When the kit is intended for analysis of hydrogen peroxide, it must contain peroxidase, aminoantipyrine and aminoaromatic acid. In such a kit, the aminoantipyrine and the aminoaromatic acid are desirably packaged separately. The peroxidase may be packed separately or admixed with either or both of these components. Similarly, if the kit is intended for analysis of blood components, additional enzymes, desirably in dry form, are included as additional components, which may be packaged separately or in a mixture with one or more of the other components. It is also desirable that the kit include a buffer, which may be packaged separately or in admixture with one or more of the antipyrine, aminoaromatic acid and peroxidase. Alternatively, all of the solid components may be packaged as a single mixture. Although less desirable, one or more of the components may be packaged in the form of an aqueous solution, either as a concentrate or at about working concentration.

When the kit is to be employed in an analysis, the components are mixed together, dissolved in or diluted with water as necessary, and employed to effect the intended analysis by generally known techniques. That is, the various ingredients are mixed with the solution to be analyzed, and the resulting mixture is held at a predetermined temperature to permit the dye of this invention to form. The concentration of the dye is then determined, as by conventional photometric analysis. Such analyses may be performed manually or automatically using equipment and techniques already well known to the art, and accordingly no further discussion of technique will be presented here.

The following examples are illustrative of the present invention, and in particular of the use of the present invention for the determination of components of body fluids.

EXAMPLE I

Uric Acid Analysis (Manual)

An aqueous solution was prepared which contained 200 units per liter of uricase, 1400 units per liter of peroxides, 0.35 millimole per liter of 4-aminoantipyrine, 100 millimoles per liter of tris buffer and 5.0 millimoles per liter of 3-(N,N-dimethylamino) benzoic acid, and which had a pH of 8. To a 2.0-ml portion of this reagent was added 50 λ of a uric acid-containing specimen at 25° C. The absorbance at 550 nm was measured immediately upon addition of the specimen to the reagent, and the absorbance was again measured after 6 minutes. The uric acid concentration was calculated by the following equation:

$$C_{ua} = \frac{\Delta A (MW_{ua}) (10^3) (TV)}{(\epsilon)(LP)(10)(SV)}$$

where $C_{ua}$ = concentration of uric acid in mg/dl.

ΔA = change in absorbance, or the difference between the absorbance after 6 minutes and the initial absorbance.

$MW_{ua}$ = the molecular weight of uric acid (168.11 Daltons).

TV = total reaction volume, ml.

LP = light path, cm.

ε = molar extinction coefficient of dye product. ($1.72 \times 10^4$ 1 mole$^{-1}$ cm$^{-1}$)

SV = sample volume, ml.

In the system employed, the equation reduced to $C_{ua} = 40.0 \Delta A$.

The procedure was repeated with 9 different standard uric acid specimens. For each specimen, a duplicate determination was made using "Statzyme Uric Acid" Reagent, a commercially available reagent marketed by Worthington Diagnostics Division of Millipore Corp. for uric acid analysis, and measuring the absorbance at 293 nm, for purposes of comparison. The results for the various analyses are summarized as follows:

| Specimen | Measured Concentration, mg/dl | |
|---|---|---|
| | Prior Art | This Invention |
| Aq. standard, 2 mg/dl | 1.9 | 2.0 |
| Aq. standard, 6 mg/dl | 5.9 | 6.2 |
| Aq. standard, 12 mg/dl | 11.8 | 11.7 |
| Monitrol I | 4.7 | 4.0 |
| Validate | 5.0 | 4.1 |
| SMA reference 3 | 6.7 | 6.6 |
| Stattrol refrence serum | 6.5 | 7.3 |
| Monitrol II | 8.4 | 9.2 |
| Validate A | 8.1 | 8.9 |

From the foregoing, it is seen that analyses obtained through use of the reagent of this invention are comparable to those obtained using the prior art reagent.

The reagent concentrations used in this example are optimum for the specific chemicals used. However, effective results can be obtained with the following concentrations:

| | |
|---|---|
| Uricase | ≧ 10 Units/liter. |
| Peroxidase | ≧ 50 units/liter. |
| 4-aminoantipyrine | 0.01 to 1000 millimoles/liter. |
| Tris buffer | 10 to 1000 millimoles/liter. |
| 3-(N,N-dimethyl-amino)benzoic acid | 0.1 to 50 millimoles/liter. |
| pH | 6.2–9.5. |

The analysis may be carried out at 20° C., using a reaction time of from about 1 to about 30 minutes, and preferably from about 5 to about 10 minutes, and measuring absorbance within the range of 450–650 nm. Under these conditions, the sensitivity of the analysis is 0.01 to 0.04 absorbance units per milligram percent, and in the specific example given, it was 0.025 absorbance units per milligram percent.

EXAMPLE II

Glucose Analysis (Manual)

An aqueous solution was prepared which contained 14,042 units per liter of glucose oxidase, 766 units per liter of peroxidase, 0.35 millimole per liter of 4-aminoantipyrine, 109 millimoles per liter of phosphate buffer and 1.0 millimoles per liter of 3-(N,N-dimethylamino)-benzoic acid, and which had a pH of 7. To a 3.5-ml portion of this reagent was added 10 λ of a glucose-containing specimen at 25° C. The absorbance at 550 nm was measured immediately upon addition of the specimen to the reagent, and the absorbance was again measured after 6 minutes. The glucose concentration was calculated by the following equation:

$$C_g = \frac{\Delta A (MW_g)(10^3)(TV)}{(\epsilon)(LP)(10)(SV)}$$

where $C_g$ = concentration of glucose in mg/dl.

ΔA = change in absorbance, or the difference between the absorbance after 6 minutes and the initial absorbance.

$MW_g$ = the molecular weight of glucose (180.16 Daltons).

TV = total reaction volume, ml.

LP = light path, cm.

ε = molar extinction coefficient of dye product. ($1.72 \times 10^4$ 1 mole$^{-1}$ cm$^{-1}$)

SV = sample volume, ml.

In the system employed, the equation reduced to $C_g = 367.6 \Delta A$. The sensitivity of the analysis was 0.213 absorbance units per mg percent.

The procedure was repeated with 9 different standard glucose specimens. For each specimen, a duplicate determination was made using "Statzyme Glucose 500", a commercially available reagent including sodium p-hydroxybenzoate and 4-aminoantipyrine sold by Worthington Diagnostics Division of Millipore Corp., and measuring the absorbance at 500 nm, for purposes of comparison. The results for the various analyses are summarized as follows:

| Specimen | Measured Concentration, mg/dl | |
|---|---|---|
| | Prior Art | This Invention |
| Aq. standard, 100 mg/dl | 101 | 101 |
| Aq. standard, 200 mg/dl | 201 | 205 |
| Aq. standard, 400 mg/dl | 395 | 413 |
| Monitrol I | 85 | 88 |
| Validate | 85 | 87 |
| SMA reference 5 | 215 | 193 |
| Hyland II | 189 | 190 |
| Monitrol II | 203 | 207 |
| Validate A | 237 | 238 |

From the foregoing, it is seen that analyses obtained through use of the reagent of this invention are comparable to those obtained using the prior art reagent.

The reagent concentrations used in this example are optimum for the specific chemicals used. However, effective results can be obtained with the following concentrations:

| | |
|---|---|
| Glucose oxidase | ≧ 100 units/liter. |
| Peroxidase | ≧ 50 units/liter. |
| 4-aminoantipyrine | 0.01 to 1000 millimoles/liter. |
| Phosphate Buffer | 10 to 1000 millimoles/liter. |
| 3-(N,N-dimethylamino) benzoic acid | 0.1 to 50 millimoles/liter. |
| pH | 4.0–9.5. |

The analyses may be carried out at 20° C. to 45° C., using a reaction time of from about 1 to about 30 minutes, and preferably from about 5 to about 10 minutes, and measuring the absorbance at 450–650 nm.

EXAMPLE III

An aqueous solution was prepared which contains 600 units per liter of cholesterol esterase, 110 units per liter of cholesterol oxidase, 1400 units per liter of peroxidase, 0.5 millimole per liter of 4-aminoantipyrine, 100 millimoles per liter of tris buffer, 5.0 millimoles per liter of 3-(N,N-dimethylamino) benzoic acid, and 0.2 percent of Triton X-100, and which had a pH of 7.5. To a 3.0-ml portion of this reagent was added 10 λ of a cholesterol-containing specimen at 30° C. The absorbance at 550 nm was measured immediately upon addition of the specimen to the reagent, and the absorbance was again measured at 15 minutes. The cholesterol concentration was calculated by the following equation:

$$C_c = \frac{\Delta A (MW_c)(10^3)(TV)}{(\epsilon)(LP)(10)(SV)}$$

where $C_c$ = concentration of cholesterol in mg/dl.
$\Delta A$ = change in absorbance, or the difference between the absorbance after 15 minutes and the initial absorbance.
$MW_c$ = the molecular weight of cholesterol (386.6 Daltons).
$TV$ = total reaction volume, ml.
$LP$ = light path, cm. $\epsilon$ = molar extinction coefficient of dye product. $(1.72 \times 10^4 \text{ 1 mole}^{-1} \text{ cm}^{-1})$
$SV$ = sample volume, ml.

In the system employed, the equation reduced to $C_c = 674.3 \Delta A$.

The procedure was repeated with 7 different standard cholesterol specimens. For each specimen, a duplicate determination was made using "Statzyme Cholesterol" Reagent, a commercially available reagent including phenol and 4-aminoantipyrine, sold by Worthington Diagnostics Division of Millipore Corp., and measuring the absorbance at 500 nm, for purposes of comparison. The results for the various analyses are summarized as follows:

| Specimen | Measured Concentration, mg/dl | |
|---|---|---|
| | Prior Art | This Invention |
| Aq. standard, 100 mg/dl | 93 | 81 |
| Aq. standard, 300 mg/dl | 250 | 302 |
| Aq. standard, 500 mg/dl | 437 | 553 |
| Scale 1 | 101 | 94 |
| Scale 2 | 194 | 148 |
| Ortho abnormal | 135 | 73 |
| Stattrol reference serum | 126 | 121 |

From the foregoing, it is seen that analyses obtained through use of the reagent of this invention are generally comparable to those obtained using the prior art reagent. There is not as good agreement as in the prior determinations, but it is believed that further optimization would lead to improvement. In particular, it is believed that optimization of the cholesterol esterase concentration would lead to results in much better agreement with those obtained with the reagent of the prior art. It should be noted, however, that in the case of the first three specimens, the reagent of this invention generally give results which were closer to the known cholesterol concentration than the results obtained with the reagent of the prior art.

The reagent concentrations used in this example are the best used so far for the specific chemicals used. However, effective results can be obtained with the following concentrations:

| Cholesterol esterase | ≧ 20 units/liter. |
|---|---|
| Cholesterol oxidase | ≧ 1 unit/liter. |
| Peroxidase | ≧ 50 units/liter. |
| 4-aminoantipyrine | 0.01 to 1000 millimoles/liter. |
| Tris buffer | 10 to 1000 millimoles/liter. |
| 3-(N,N-dimethylamino)-benzoic acid | 0.1 to 50 millimoles/liter. |
| Triton X-100 | 0.001–10 percent. |
| pH | 3–9. |

The analysis may be carried out at 20° C. to 45° C., using a reaction time of from about 1 to about 45 minutes, and preferably from about 10 to about 20 minutes, and measuring absorbance within the range of 450–650 nm. Under these conditions, the sensitivity of the analysis is 0.1 to 0.4 absorbance units per milligram percent and in the specific example given, it was 0.150 absorbance units per milligram percent.

EXAMPLE IV

Uric Acid Analysis (Automated)

Three aqueous solutions were prepared: (1) An enzyme reagent solution containing 200 units per liter of uricase, 1400 units per liter of peroxidase, 0.35 millimoles per liter of 4-aminoantipyrine and 100 millimoles per liter of tris buffer; (2) a chromophore-buffer solution containing 5.0 millimoles per liter of 3-(N,N-dimethylamino)benzoic acid and 100 millimoles per liter of tris buffer; and (3) a sample buffer solution containing 100 millimoles per liter of tris buffer. The pH of each solution was 8.0.

These solutions were employed to determine uric acid concentration in the same 9 samples employed in Example I, except that an automated procedure using a Technicon Type II Auto Analyzer equipped with a 12-inch dialyzer containing a type C membrane, at a sampling rate of 60 per hour and a sample/wash ratio of 9:1 (6 sec. wash time). A stream of the sample buffer, containing 1 ml/l of Brij 35 surfactant is fed to one surface of the analyzer membrane at a rate of 1 cc per minute; after admixing with the sample being analyzed fed at a rate of 0.32 cc per minute and air at 0.32 cc per minute. A mixture of the enzyme reagent solution containing 1 ml/l of Brij 35, (0.23 cc/min) and the chromophore-buffer solution (100 cc/m), after mixing with air fed at a rate of 0.32 cc/min, is fed to the other side of the membrane of the dialyzer.

The absorbance of the samples were determined in a 1.5 cm flow cell using a 550 nm filter, and a pull through of 1.0 cc/min. after 5-½ minutes of incubation. The sensitivity of the method was about 0.017 absorbance units per milligram percent uric acid. Results were automatically recorded by a strip chart recorder and a concentration calculator, on the basis of a standard calibrator serum with a known uric acid concentration.

The results are summarized below, together with the results obtained with this invention in Example I employing the manual procedure:

| | Uric Acid Concentration | |
|---|---|---|
| Specimen | Manual (Example I) | Automated |
| Aq. standard, 2 mg/dl | 2.0 | 2.2 |
| Aq. standard, 6 mg/dl | 6.2 | 7.0 |
| Aq. standard, 12 mg/dl | 11.7 | 13.2 |
| Monitrol I | 4.0 | 4.5 |
| Validate | 4.1 | 4.2 |
| SMA reference 3 | 6.6 | 6.7 |
| Stattrol reference serum | 7.3 | 7.4 |
| Monitrol II | 9.2 | 8.9 |
| Validate A | 8.9 | 7.5 |

In general, the results obtained with the reagent of this invention in an automated procedure were in reasonable agreement with those obtained using the reagent of this invention in a manual procedure.

Effective results can be obtained with this automated procedure employing reagents having the following compositions:

| Enzyme Reagent | |
|---|---|
| Uricase | ≧ 10 units/liter. |
| Peroxidase | ≧ 50 units/liter. |
| 4-Aminoantipyrine | 0.01 to 1000 millimoles/liter. |
| Tris Buffer | 10 to 1000 millimoles/liter. |
| Chromophore-Buffer | |
| 3-(N,N-dimethylamino)-benzoic acid | 0.1 to 50 millimoles/liter. |
| Tris Buffer | 10 to 1000 millimoles/liter. |
| Sample Buffer | |
| Tris Buffer | 10 to 1000 millimoles/liter. |

The procedure can be carried out at a temperature of 20° C. to 45° C., a pH of 6.2-9.5 and a reaction time of 1-30 minutes, measuring absorbance at 450-650 nm, at a sensitivity of 0.01 to 0.4 absorbance units per milligram percent.

As is evident from the foregoing examples, small amounts of surfactants may be employed. Surfactants are especially desirable in performing automated analyses as illustrated by Example IV.

What is claimed is:

1. A method for producing a dye comprising contacting, in an aqueous medium at a temperature of from about 20° to about 45° C., having a pH of from about 3 to about 9.5, and containing hydrogen peroxide, (1) peroxidase, (2) an amino-aromatic acid represented by the formula:

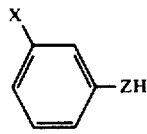

wherein X is a mono- or dialkylamino group, and ZH is the carboxyl group or the sulfo group, and (3) a 4-aminoantipyrine represented by the formula:

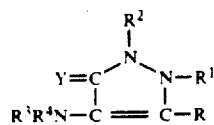

wherein each of R and $R^1$, when taken separately, is alkyl, $R^2$ is an aromatic moiety, each of $R^3$ and $R^4$, when taken separately, is hydrogen or alkyl, and Y is oxygen or sulfur, wherein the molar ratio of said aminoaromatic acid to said aminoantipyrine is in th range of from bout 0.1:1 to about 25:1.

2. A method according to claim 1 wherein said aminoaromatic acid is an aminobenzoic acid and said aminoantipyrine is one wherein $R^2$ is phenyl and Y is oxygen.

3. A method according to claim 2 wherein said aminoantipyrine is one wherein R and $R^1$ each is methyl.

4. A method according to claim 3 wherein said aminobenzoic acid is 3-(N,N-dimethylamino)benzoic acid.

5. A method according to claim 4 wherein said aminoantipyrine is one wherein each of $R^3$ and $R^4$ is hydrogen.

6. A method according to claim 4 wherein said aminoantripyrine is one wherein each of $R^3$ and $R^4$ is methyl.

7. A method according to claim 5 wherein the molar ratio of said 3-(N,N-dimethylamino)benzoic acid to said aminoantipyrine is in the range of from about 8:1 to about 12:1.

8. A method for detecting the presence of hydrogen peroxide in an aqueous medium at a temperature of from about 20° C. to about 45° C. and having a pH of from about 3 to about 9.5, which comprises: (a) adding to said aqueous medium (1) peroxidase, (2) an aminoaromatic acid represented by the formula:

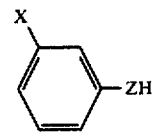

wherein X is a mono-or dialkylamine group and ZH is the carboxyl group or the sulfo group, and (3) a 4-aminoantipyrine represented by the formula:

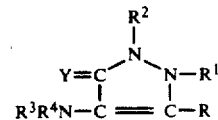

wherein each of R and $R^1$, when taken separately, is alkyl, $R^2$ is an aromatic moiety, each of $R^3$ and $R^4$, when taken separately, is hydrogen or alkyl, and Y is oxygen or sulfur, wherein the molar ratio of said aminoaromatic acid to said aminoantipyrine is in the range of from about 0.1:1 to about 25:1; and (b) thereafter measuring any resulting color change photometrically.

9. A method according to claim 8 wherein said aminoaromatic acid is an aminobenzoic acid and said aminoantipyrine is one wherein $R^2$ is phenyl and Y is oxygen.

10. A method according to claim 9 wherein said aminoantipyrine is one wherein each of R and $R^1$ is methyl.

11. A method according to claim 10 wherein said aminobenzoic acid is 3-(N,N-dimethylamino)benzoic acid.

12. A method according to claim 11 wherein said aminoantipyrine is one wherein each of $R^3$ and $R^4$ is hydrogen.

13. A method according to claim 11 wherein said aminoantipyrine is one wherein each of $R^3$ and $R^4$ is methyl.

14. A method according to claim 12 wherein the molar ratio of said 3-(N,N-dimethylamino)-benzoic acid to said aminoantipyrine is in the range of from about 8:1 to about 12:1.

15. In a method for the enzymatic determination of the amount of a component in a body fluid by admixing said fluid with (a) an enzyme capable of promoting the oxidation of said component and forming hydrogen peroxide, (b) peroxidase, and (c) a chromagen capable of being oxidized by peroxidasecatalyzed reaction with hydrogen peroxide to form a chromophore, and measuring the resulting color change, the improvement wherein said chromogen is a mixture of (1) an aminoaromatic acid represented by the formula:

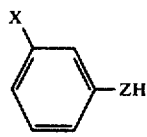

wherein X is a mono- or dialkyl amine group and ZH is the carboxyl or the sulfo group and (2) a 4-aminoantipyrine represented by the formula:

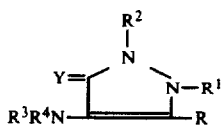

wherein each of R and $R^1$, when taken separately, is alkyl, $R^2$ is an aromatic moiety, each of $R^3$ and $R^4$, when taken separately, is hydrogen or alkyl, and Y is oxygen or sulfur, wherein the molar ratio of said aminoaromatic acid to said aminoantipyrine is in the range of from about 0.1:1 to about 25:1, said method being conducted at a temperture of from about 20° C. to about 45° C., and a pH of from about 3 to about 9.5.

16. A method according to claim 15 wherein said aminoaromatic acid is an aminobenzoic acid and said aminoantipyrine is one wherein $R^2$ is phenyl and Y is oxygen.

17. A method according to claim 16 wherein sid aminoantipyrine is one wherein each of R and $R^1$ is methyl.

18. A method according to claim 17 wherein said aminobenzoic acid is 3-(N,N-dimethylamino)benzoic acid.

19. A method according to claim 18 wherein said aminoantipyrine is one wherein each of $R^3$ and $R^4$ is hydrogen.

20. A method according to claim 18 wherein said aminoantipyrine is one wherein each of $R^3$ and $R^4$ is methyl.

21. A method according to claim 19 wherein the molar ratio of said 3-(N,N-dimethylamino)-benzoic acid to said aminoantipyrine is in the range of from about 8:1 to about 12:1.

22. A method according to claim 15 wherein said enzyme capable of promoting oxidation of said component is uricase.

23. A method according to claim 15 wherein said enzyme capable of promoting oxidation of said component is glucose oxidase.

24. A method according to claim 15 wherein said enzyme capable of promoting oxidation of said component is cholesterol oxidase.

25. A reagent system for detecting the presence of hydrogen peroxide in an aqueous medium comprising: (1) peroxidase, (2) an aminoaromatic acid represented by the formula:

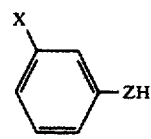

wherein X is a mono- or dialkylamino group and ZH is the carboxyl group or the sulfo group, and (3) a 4-aminoantipyrine represented by the formula:

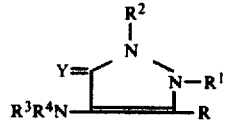

wherein each of R and $R^1$, when taken separately, is alkyl, $R^2$ is an aromatic moiety, each of $R^3$ and $R^4$, when taken separately, is hydrogen or alkyl, and Y is oxygen or sulfur, wherein the molar ratio of said aminoaromatic acid to said aminoantipyrine is from about 0.1:1 to about 25:1.

26. A system according to claim 25 additionally including a buffer to buffer an aqueous solution of said peroxidase, aminoaromatic acid and aminoantipyrine to a pH in the range of from about 3 to about 9.5.

27. A system according to claim 26 additionally including an enzyme capable of supporting oxidation of a component of a body fluid to form hydrogen peroxide.

28. A system according to claim 27 wherein said enzyme is capable of supporting the oxidation of uric acid, cholesterol or glucose to form hydrogen peroxide.

29. A system according to claim 27 wherein ZH is carboxyl, $R^2$ is phenyl and Y is oxygen.

30. A system according to claim 29 wherein X is aminoalkyl, R is methyl and $R^1$ is methyl.

31. A system according to claim 30 wherein X is dimethylamino and $R^3$ and $R^4$ each is methyl.

32. A system according to claim 30 wherein X is dimethylamino and $R^3$ and $R^4$ each is hydrogen.

33. A system according to claim 32 wherein the molar ratio of said aminoaromatic acid to said aminoantipyrine is in the range of from about 8:1 to about 12:1.

34. A system according to claim 33 wherein said enzyme capable of supporting oxidation is uricase.

35. A system according to claim 33 wherein said enzyme capable of supporting oxidation is glucose oxidase.

36. A system according to claim 33 wherein said enzyme capable of supporting oxidation is cholesterol oxidase.

37. The system according to claim 25 in kit form.

* * * * *